US009353076B2

(12) United States Patent
Li et al.

(10) Patent No.: US 9,353,076 B2
(45) Date of Patent: May 31, 2016

(54) CRYSTAL FORM OF CABAZITAXEL AND PREPARATION METHOD THEREOF

(71) Applicant: Chongqing Taihao Pharmaceutical Co., Ltd., Chongqing (CN)

(72) Inventors: Jing Li, Chongqing (CN); Quanxing Yao, Chongqing (CN)

(73) Assignee: CHONGQING TAIHAO PHARMACEUTICAL CO., LTD., Chongqing (CN)

( * ) Notice: Subject to any disclaimer, the term of this patent is extended or adjusted under 35 U.S.C. 154(b) by 0 days.

(21) Appl. No.: 14/399,513

(22) PCT Filed: Jul. 18, 2013

(86) PCT No.: PCT/CN2013/079575
§ 371 (c)(1),
(2) Date: Nov. 7, 2014

(87) PCT Pub. No.: WO2014/015760
PCT Pub. Date: Jan. 30, 2014

(65) Prior Publication Data
US 2015/0141674 A1    May 21, 2015

(30) Foreign Application Priority Data

Jul. 25, 2012 (CN) .......................... 2012 1 0259595

(51) Int. Cl.
*C07D 305/14* (2006.01)
(52) U.S. Cl.
CPC ........... *C07D 305/14* (2013.01); *C07B 2200/13* (2013.01)
(58) Field of Classification Search
CPC .................................................... C07D 305/14
See application file for complete search history.

(56) References Cited

U.S. PATENT DOCUMENTS

| 8,901,322 | B2 * | 12/2014 | Lahiri et al. | 549/351 |
| 9,012,665 | B2 * | 4/2015 | Kung et al. | 549/510 |
| 2002/0048610 | A1 | 4/2002 | Cima et al. | |
| 2005/0065138 | A1 | 3/2005 | Didier et al. | |
| 2011/0144362 | A1 | 6/2011 | Billot et al. | |
| 2013/0109870 | A1 * | 5/2013 | Lahiri et al. | 549/510 |
| 2013/0211109 | A1 | 8/2013 | Lahiri et al. | |
| 2014/0350272 | A1 | 11/2014 | Billot et al. | |

FOREIGN PATENT DOCUMENTS

| CN | 100429207 C | 10/2008 |
| CN | 101525321 A | 9/2009 |
| CN | 101918385 A | 12/2010 |
| CN | 102060815 A | 5/2011 |
| CN | 102336726 A | 2/2012 |
| CN | 102482243 A | 5/2012 |
| CN | 102503913 A | 6/2012 |
| CN | 102746258 A | 10/2012 |
| CN | 102898406 A | 1/2013 |
| CN | 103058960 A | 4/2013 |
| CN | 103814018 A | 5/2014 |
| JP | 2003519698 A | 6/2003 |
| JP | 2007505866 A | 3/2007 |
| JP | 2011509980 A | 3/2011 |
| WO | 2005028462 A1 | 3/2005 |
| WO | 2009115655 A2 | 9/2009 |
| WO | 2012142117 A1 | 10/2012 |
| WO | 2013034979 A2 | 3/2013 |
| WO | 2013080217 A2 | 6/2013 |
| WO | 2013088335 A1 | 6/2013 |
| WO | 2013134534 A2 | 9/2013 |

OTHER PUBLICATIONS

Cabazitaxel, 2015, http://www.cancer.gov/about-cancer/treatment/drugs/fda-cabazitaxel.*
Breast-Cancer, 2015, http://www.cancer.org/cancer/breastcancer/overviewguide/breast-cancer-overview-prevention.*
Prevent-Cancer, 2015, http://www.medicinenet.com/cancer/page9.htm.*
International Search Report for PCT/CN2012/084293.
Beiqi Ma, "US FDA Approved Cabazitaxel to Treat Hormone-refractory Metastatic Prostate Cancer for Secondary Prophylaxis", China Academic Journal Electronic Publishing House 2010, vol. 31, Nov. Issue, 2 pages.
Guoning Zhang et al., "A new synthesis route of cabazitaxel", Journal of Chinese Pharmaceutical Sciences 21 (2012) 472-476 , 5 pages.
The Partial European search report issued on Aug. 4, 2015 regarding a European counterpart application (EP 13822828).
Yoko Kawaguchi et al., "Drug and Crystal Polymorphism", Journal of Human Environmental Engineering, 2002, vol. 4, pp. 310-317.

(Continued)

*Primary Examiner* — Sun Jae Yoo
(74) *Attorney, Agent, or Firm* — Kilpatrick Townsend & Stockton LLP

(57) ABSTRACT

The present invention relates to the field of medical chemistry, and discloses a preparing method for three crystal forms of cabazitaxel, that is, crystalline form J of cabazitaxel esterate, crystalline form G of cabazitaxel hydrate and crystalline form I of cabazitaxel, and a novel crystalline form of cabazitaxel. The novel crystalline form of cabazitaxel according to the invention has good stability and good solubility in commonly used solvents, and is easy to be preserved and is stable under treatment during preparation of dosage forms, thus could be used for the preparation of a medicament for treating prostate cancer.

7 Claims, 6 Drawing Sheets

(56) References Cited

OTHER PUBLICATIONS

Evaluation and Licensing Div., PMSB, Notification No. 568, 2001.
Ooshima Hiroshi, "Crystallization of Polymorphs and Pseudopolymorphs and Its Control", Pharm Stage 2007, vol. 6, No. 10, pp. 48-53.
Noriyuki Takada, "API form screening and selection in drug discovery stage", Pharm Stage 2007, vol. 6, No. 10, pp. 20-25.
Mitsuhisa Yamano, "Approach to Crystal Polymorph in Process Research of New Drug", Journal of Synthetic Organic Chemishy, 2007, vol. 65, No. 9, p. 907-913.
Stephen Byrn et al., "Pharmaceutical Solids: A Strategic Approach to Regulatory Considerations", Pharmaceutical Research 1995, vol. 12, pp. 945-954.
The first Office Action issued on Jan. 8, 2016 regarding a Japanese counterpart application (JP 2015514346).

* cited by examiner

CRYSTAL FORM OF CABAZITAXEL AND PREPARATION METHOD THEREOF

The present application is the national phase of International Application No. PCT/CN2013/079575, titled "CRYSTAL FORM OF CABAZITAXEL AND PREPARATION METHOD THEREOF", filed on Jul. 18, 2013, which claims the benefits of priorities to Chinese Patent Application No. 201210259595.3, titled "CRYSTAL FORM OF CABAZITAXEL AND PREPARATION METHOD THEREOF", filed with the Chinese State Intellectual Property Office on Jul. 25, 2012, both of which applications are incorporated herein in their entireties by this reference.

FIELD OF THE INVENTION

The present invention relates to the field of medical chemistry, and in particular to a novel crystalline form of Cabazitaxel and preparation method thereof.

BACKGROUND OF THE INVENTION

Cabazitaxel, 4-acetoxy-2α-benzoyloxy-5β,20-epoxy-1-hydroxy-7β,10β-dimethoxy-9-oxo-11-taxadiene-13α-yl (2R,3S)-3-tert-butoxycarbonylamino-2-hydroxy-3-phenyl-propionate, has the structure as represented by formula (I):

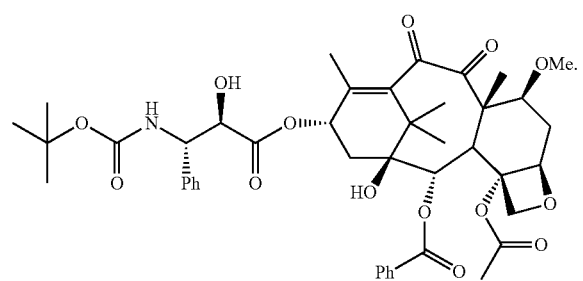

Cabazitaxel is a semi-synthetic taxoid small molecule compound developed by Sanofi-aventis, France. It is a second line treatment for prostate cancer and is approved to be marketed in America in June, 2010.

Cabazitaxel has similar anti-cancer mechanism and feature with docetaxel, both are anti-microtubule drugs. The binding of Cabazitaxel to tubulin promotes the assembly of tubulin into microtubules and simultaneously inhibits disassembly, and thereby stabilizing microtubule dynamics, and in turn, blocking mitosis and interphase cellular functions. Cabazitaxel is used for a patient with advanced prostate cancer who does not respond to docetaxel and even with worsened condition. It is a leading choice for the treatment of advanced, hormone-refractory prostate cancer. Cabazitaxel injection solution is used in combination with prednisone for treatment of patients with metastatic hormone-refractory prostate cancer (mHRPC) previously treated with a docetaxel-containing regimen.

Crystalline form is one of the influential factors that affect the quality, therapeutic efficacy and processing property of a medicine. Polymorphism refers to the occurrence of two or more types of molecular conformation of a same compound by controlling the formation condition, and thereby forming different solid crystalline forms. Polymorphism, which is common in the development of a medicine, is an influential factor for the quality of a pharmaceutical product. Different crystalline forms of a same compound exhibit the same composition, but different crystalline microscopic structures. Thus, polymorphs of a compound can differ in morphologic appearance, physicochemical properties and biological activity. These properties directly influence processing property, stability, solubility and bioavailability, and in turn, quality, safety, efficacy and application of a medicine. Therefore, there is a need to comprehensively consider the polymorphism issue in the development of a pharmaceutical product.

Currently, Cabazitaxel is known to give rise to a variety of crystalline forms. Patent WO2005/028462 identifies and characterizes a crystalline form A of Cabazitaxel, i.e., the acetone solvate of 4-acetoxy-2α-benzoyloxy-5β,20-epoxy-1-hydroxy-7β,10β-dimethoxy-9-oxo-11-taxadiene-13α-yl (2R,3S)-3-tert-butoxycarbonylamino-2-hydroxy-3-phenyl-propionate. Patent WO2009/115655 identifies and characterizes anhydrate forms B, C, D, E and F, ethanolate forms B, D and E, ethanol/water hetero-solvate F, monohydrate form C and dihydrate form C of Cabazitaxel.

SUMMARY OF THE INVENTION

In view of the above, an object of the present invention is to study, discover and provide a novel crystalline form of Cabazitaxel and the preparing method thereof by crystallinelography.

First, the present invention studies, discovers and provides three crystalline forms of Cabazitaxel by crystallinelography, that is, crystalline form J of Cabazitaxel esterate, crystalline form G of Cabazitaxel hydrate and crystalline form I of Cabazitaxel.

A novel crystalline form of Cabazitaxel may be studied and characterized by, for example, the internationally recognized X-ray powder diffraction (XRPD) in accordance with the present invention. For example, the following condition may be used: Instrument: RIGAKU TTR III X-ray powder diffractometer; Measurement: Cu/K-alpha1 (target), 40 KV-200 mA (operating voltage and current), I (max)=2244, 2θ=5-60° (scan range), 0.005/0.06 sec. (scan speed), λ=1.54056.

According to an aspect of the present invention, a crystalline form J of Cabazitaxel esterate is provided. In one embodiment, the crystalline form J of Cabazitaxel esterate can be characterized by an X-ray powder diffraction pattern having peaks at 2θ of about 7.9, 8.5, 10.1, 12.6, 14.0, 15.0, 15.8, 17.3, 19.4, 20.1 and 22.4 degrees. Preferably, the corresponding peak intensities are 100.0, 7.9, 21.6, 14.1, 33.7, 26.5, 23.3, 19.1, 23.3, 37.4 and 18.6. More preferably, the X-ray powder diffraction pattern is shown in FIG. 1.

In another embodiment, the present invention further studies and characterizes a novel crystalline form of Cabazitaxel with infrared spectrometry (IR). For example, the following condition may be used: Instrument: BRUKER TENSOR27 Fourier Transform Infrared Spectrometer (Bruker, German); Measurement: KBr disk, spectrum range: 400 $cm^{-1}$-4000 $cm^{-1}$, resolution: 4 $cm^{-1}$.

Preferably, an infrared spectrum pattern for the crystalline form J of Cabazitaxel esterate provided by the present invention is shown in FIG. 2.

In another embodiment, other analysis technologies known in the art may be used to characterize the crystalline form J. For example, the crystalline form J of Cabazitaxel esterate can be characterized by a thermogravimetric analysis (TGA) pattern as shown in FIG. 3, and by a differential scanning calorimetry (DSC) pattern as shown in FIG. 4.

According to another aspect of the present invention, a crystalline form G of Cabazitaxel hydrate is provided. In one embodiment, the hydrate crystalline form G can be characterized by a powder X-ray diffraction pattern having peaks at 2θ of about 4.5, 8.5, 8.9, 11.1, 12.4, 13.9, 15.4, 17.7 and 19.3 degrees. Preferably, the corresponding peak intensities are 19.0, 42.1, 100, 36.5, 9.2, 26.5, 19.8, 41.8 and 25.3. More preferably, the X-ray powder diffraction pattern is shown in FIG. 5.

In another embodiment, an infrared spectrum pattern for the crystalline form G of Cabazitaxel hydrate is shown in FIG. 6, a thermogravimetric analysis (TGA) pattern is shown in FIG. 7, and a differential scanning calorimetry (DSC) pattern is shown in FIG. 8.

According to another aspect of the present invention, a crystalline form I of Cabazitaxel is further provided. In one embodiment, the crystalline form I can be characterized by an X-ray powder diffraction pattern having peaks at 2θ of about 7.4, 7.8, 8.9, 10.1, 14.4, 15.0, 15.7, 17.7, 19.6 and 23.5 degrees. Preferably, the corresponding peak intensities are 20.1, 100, 13.1, 11.5, 44.2, 10.7, 10.2, 17.7, 24.4 and 16.4. More preferably, the powder X-ray diffraction pattern is shown in FIG. 9.

In another embodiment, an infrared spectrum pattern for a crystalline form I of Cabazitaxel is shown in FIG. 10.

It should be noted that, in terms of the powder X-ray diffraction peaks of the crystalline forms above, 2θ of the powder X-ray diffraction pattern may give rise to a slightly change between one machine and another, as well as one sample and another. The numerical values thereof may differ by about one unit, or about 0.8 unit, or about 0.5 unit, or about 0.3 unit, or about 0.1 unit. Thus, the given numerical values should not be considered as absolute.

The experimental results indicate that, the crystalline form J of Cabazitaxel esterate, the crystalline form G of Cabazitaxel hydrate and crystalline form I of Cabazitaxel have good property in terms of solubility, and thereby have high bioavailability.

According to a further aspect of the present invention, a process for the preparation of a novel crystalline form of Cabazitaxel in an industrial scale is provided.

In one embodiment, the present invention provides a method for preparing a crystalline form J of Cabazitaxel esterate, comprising: dissolving Cabazitaxel in an ester compound with 1 to 6 carbon atoms, and crystallizing from the solution to thereby obtain the crystalline form J of Cabazitaxel esterate.

Preferably, a method for preparing a crystalline form J of Cabazitaxel esterate comprises: dissolving Cabazitaxel in an ester compound with 1 to 6 carbon atoms, followed by concentrating, crystallizing, suction filtrating and cake drying to thereby obtain the crystalline form J of Cabazitaxel esterate.

More preferably, the concentrating is performed till viscous or a suitable amount of crystalline precipitated. Then, crystallizing at low temperature, suction filtering and cake drying by heating are performed to obtain the crystalline form J of Cabazitaxel esterate.

In a preferred embodiment, in the method for preparing a crystalline form J of Cabazitaxel esterate, the amount of an ester compound with 1 to 6 carbon atoms used, expressed in g/mL, is preferably 1 to 50 times greater than Cabazitaxel. That is, 1 to 50 mL of an ester compound with 1 to 6 carbon atoms is added for per g Cabazitaxel. An amount of 20 to 30 times greater than Cabazitaxel is more preferred.

In another preferred embodiment, in the method for preparing a crystalline form J of Cabazitaxel esterate, the ester compound with 1 to 6 carbon atoms is methyl formate, ethyl acetate or diethyl malonate, more preferably, ethyl acetate or methyl formate.

In another embodiment, the present invention provides a method for preparing a crystalline form G of Cabazitaxel hydrate, comprising: dissolving Cabazitaxel in halogenated alkanes with 1 to 5 carbon atoms or alcohol compounds with 1 to 4 carbon atoms and adding water, or dissolving Cabazitaxel in a mixture of halogenated alkanes with 1 to 5 carbon atoms and water or a mixture of alcohol compounds with 1 to 4 carbon atoms and water; and crystallizing from the solution to thereby obtain the crystalline form G of Cabazitaxel hydrate. The step of dissolving Cabazitaxel in a mixture of halogenated alkanes with 1 to 5 carbon atoms and water or a mixture of alcohol compounds with 1 to 4 carbon atoms and water refers to, firstly, mixing halogenated alkanes with 1 to 5 carbon atoms or alcohol compounds with 1 to 4 carbon atoms with water, and then, dissolving Cabazitaxel in the mixture.

Preferably, a method for preparing a crystalline form G of Cabazitaxel hydrate comprises: dissolving Cabazitaxel in halogenated alkanes with 1 to 5 carbon atoms or alcohol compounds with 1 to 4 carbon atoms and adding water, or dissolving Cabazitaxel in a mixture of halogenated alkanes with 1 to 5 carbon atoms and water or a mixture of alcohol compounds with 1 to 4 carbon atoms and water; followed by crystallizing, suction filtering and cake drying to thereby obtain the crystalline form G of Cabazitaxel hydrate.

More preferably, the crystallizing is performed at low temperature. The cake drying is performed by heating.

In a preferred embodiment, in the method for preparing a crystalline form G of Cabazitaxel hydrate, the amount of the halogenated alkanes with 1 to 5 carbon atoms or alcohol compounds with 1 to 4 carbon atoms used, expressed in g/mL, is preferably 5 to 40 times greater than Cabazitaxel. That is, 5 to 40 mL of halogenated alkanes with 1 to 5 carbon atoms or alcohol compounds with 1 to 4 carbon atoms are added for per g Cabazitaxel. An amount of 8 to 20 times greater than Cabazitaxel is more preferred.

In another preferred embodiment, in the method for preparing a crystalline form G of Cabazitaxel hydrate, the amount of water used, expressed in g/mL, is preferably 10 to 40 times greater than Cabazitaxel. That is, 10 to 40 mL of water is added for per g Cabazitaxel. An amount of 20 to 30 times greater than Cabazitaxel is more preferred.

In another preferred embodiment, in the method for preparing a crystalline form G of Cabazitaxel hydrate, the halogenated alkanes with 1 to 5 carbon atoms are preferably methylene chloride, trichloromethane, dichloroethane, trichloroethane, chloropropane or chlorobutane, more preferably, methylene chloride or trichloromethane.

In another preferred embodiment, in the method for preparing a crystalline form G of Cabazitaxel hydrate, the alcohol compounds with 1 to 4 carbon atoms are preferably methanol, ethanol, propanol or isopropanol, more preferably, methanol or ethanol.

In another embodiment, the present invention provides a method for preparing a crystalline form I of Cabazitaxel, comprising: dissolving Cabazitaxel in methylene chloride and adding cyclohexane, or dissolving Cabazitaxel in a mixture of methylene chloride and cyclohexane; and crystallizing from the solution to thereby obtain the crystalline form I of Cabazitaxel. The step of dissolving Cabazitaxel in a mixture of methylene chloride and cyclohexane refers to, firstly, mixing methylene chloride and cyclohexane, and then, dissolving Cabazitaxel in the mixture.

Preferably, a method for preparing a crystalline form I of Cabazitaxel comprises: dissolving Cabazitaxel in methylene chloride and adding cyclohexane, or dissolving Cabazitaxel in a mixture of methylene chloride and cyclohexane, followed by crystallizing, suction filtering and cake drying to thereby obtain the crystalline form I of Cabazitaxel.

More preferably, the crystallizing is performed at low temperature. The cake drying is performed by heating.

In a preferred embodiment, in the method for preparing a crystalline form I of Cabazitaxel, the amount of methylene chloride used, expressed in g/mL, is preferably 1 to 50 times greater than Cabazitaxel. That is, 1 to 50 mL of methylene chloride is added for per g Cabazitaxel. An amount of 5 to 20 times greater than Cabazitaxel is more preferred.

In another preferred embodiment, in the method for preparing a crystalline form I of Cabazitaxel, the amount of cyclohexane used, expressed in g/mL, is preferably 2 to 100 times greater than Cabazitaxel. That is, 2 to 100 mL of cyclohexane is added for per g Cabazitaxel. An amount of 10 to 40 times greater than Cabazitaxel is more preferred.

In a preferred embodiment of the present invention, the crystalline form J of Cabazitaxel esterate, the crystalline form G of Cabazitaxel hydrate and the crystalline form I of Cabazitaxel are prepared by crystallizing at low temperature, suction filtrating and cake drying by heating.

Wherein, the temperature for crystallizing at low temperature is preferably −20 to 35° C., more preferably, −10 to 10° C.

Moreover, the temperature for the cake drying by heating is preferably 30 to 100° C., more preferably, 50 to 60° C.

The novel crystalline forms of Cabazitaxel according to the present invention has good stability and good solubility in commonly used solvents, and is easy to be preserved and is stable under treatment during preparation of dosage forms, thus could be used for the preparation of a medicament for treating prostate cancer.

The novel crystalline form of Cabazitaxel according to the present invention has good stability and solubility, allowing it to be further formulated into a suitable dosage form.

DETAILED EMBODIMENTS

Figure 1:
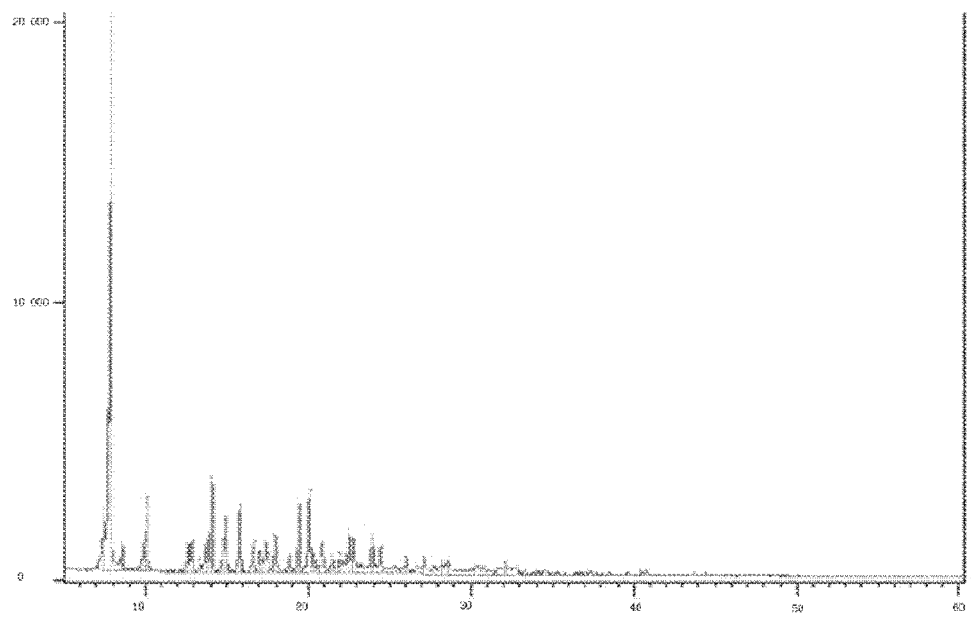
FIG. 1 shows an X-ray powder diffraction pattern for crystalline form J of Cabazitaxel solvate with ethyl acetate provided by example 1 of the present invention, which is obtained by irradiation with cooper Kα ray. In the X-ray powder diffraction pattern, the ordinate represents diffraction intensity expressed in counts per second (cps), and the abscissa represents diffraction angle 2θ expressed in degree.
Figure 2:
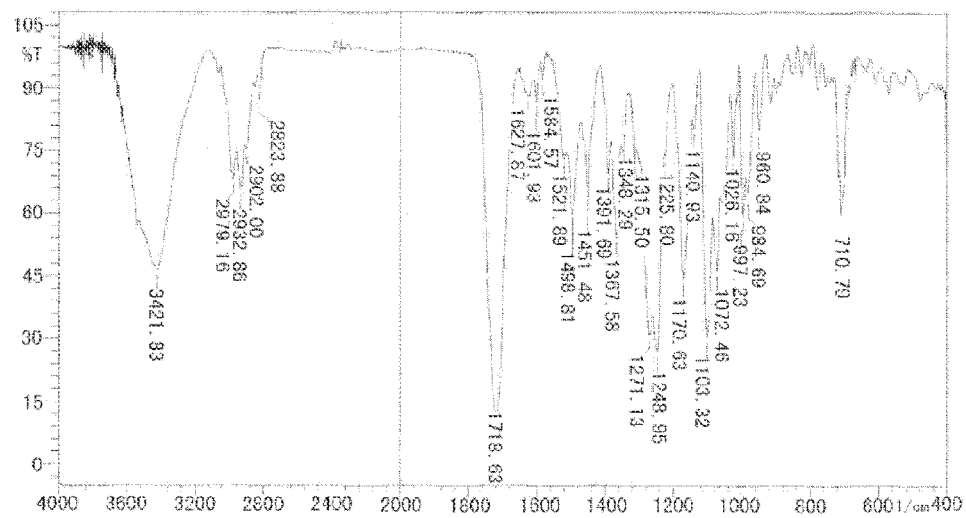
FIG. 2 shows an infrared spectrum pattern for crystalline form J of Cabazitaxel solvate with ethyl acetate provided by example 1 of the present invention. The ordinate represents light transmittance (T) expressed in percentage (%), and the abscissa represents wave number expressed in $cm^{-1}$.
Figure 3:
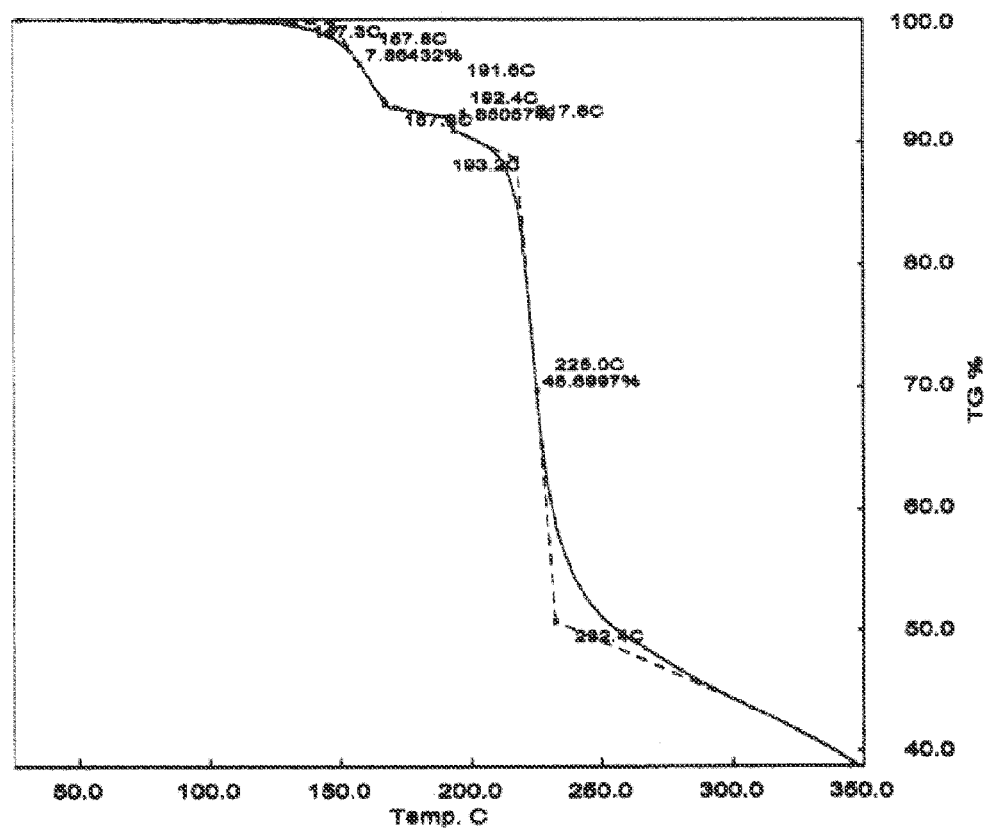
FIG. 3 shows a thermogravimetric analysis (TGA) pattern for crystalline form J of Cabazitaxel solvate with ethyl acetate provided by example 1 of the present invention. The ordinate represents weight (mg) expressed in percentage (%), and the abscissa represents temperature expressed in ° C.
Figure 4:
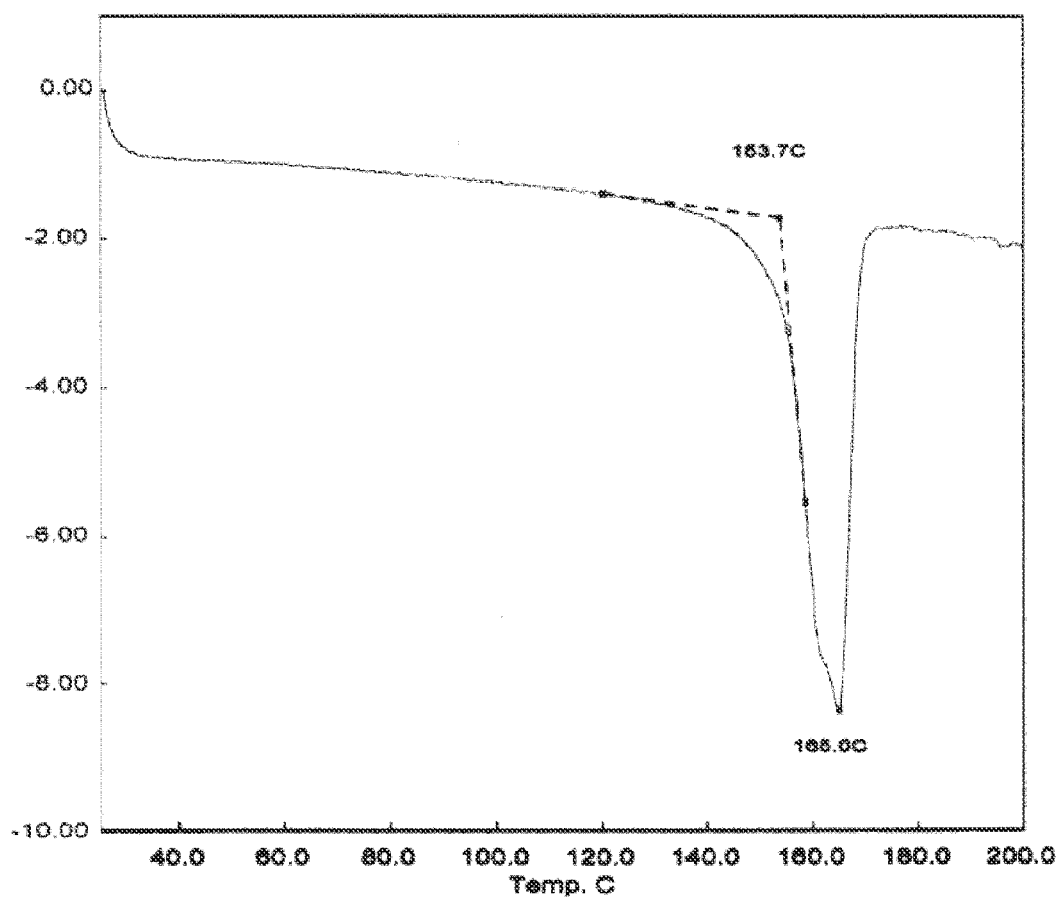
FIG. 4 shows a differential scanning calorimetry (DSC) pattern for crystalline form J of Cabazitaxel solvate with ethyl acetate provided by example 1 of the present invention. The ordinate represents rate for heat flow expressed in cal/sec, and the abscissa represents temperature expressed in ° C.
Figure 5:
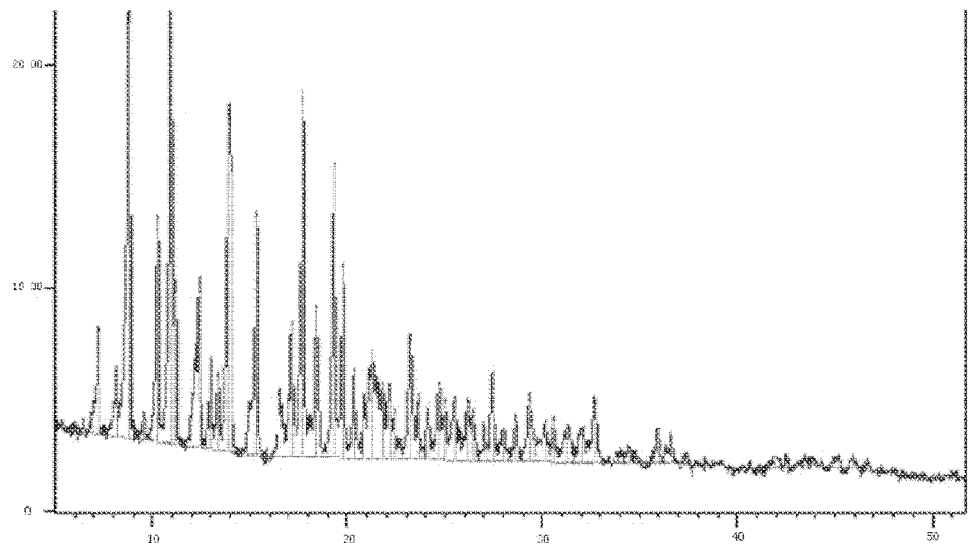
FIG. 5 shows an X-ray powder diffraction pattern for crystalline form G of Cabazitaxel hydrate provided by example 3 of the present invention, which is obtained by irradiation with cooper Kα ray. In the X-ray powder diffraction pattern, the ordinate represents diffraction intensity expressed in counts per second (cps), and the abscissa represents diffraction angle 2θ expressed in degree.
Figure 6:
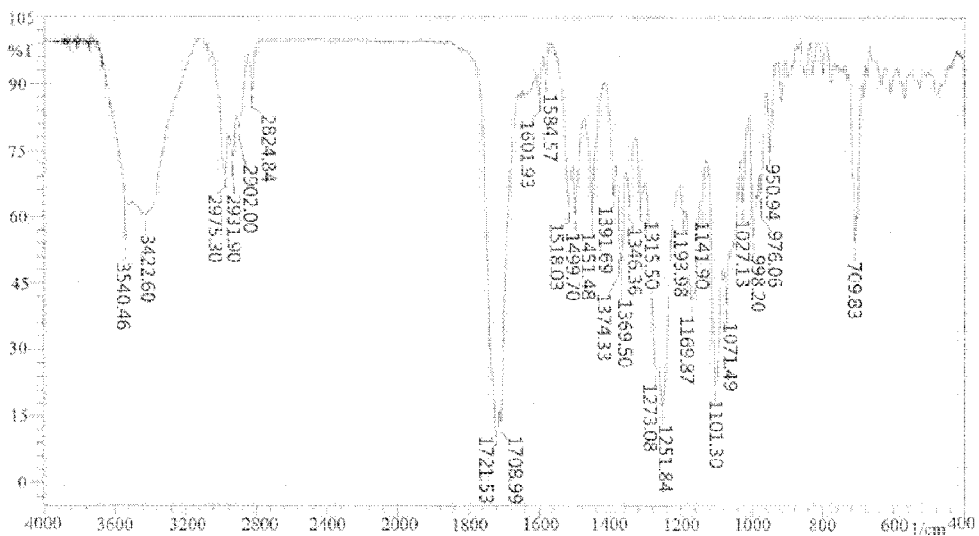
FIG. 6 shows an infrared spectrum pattern for crystalline form G of Cabazitaxel hydrate provided by example 3 of the present invention. The ordinate represents light transmittance (T) expressed in percentage (%), and the abscissa represents wave number expressed in $cm^{-1}$.
Figure 7:
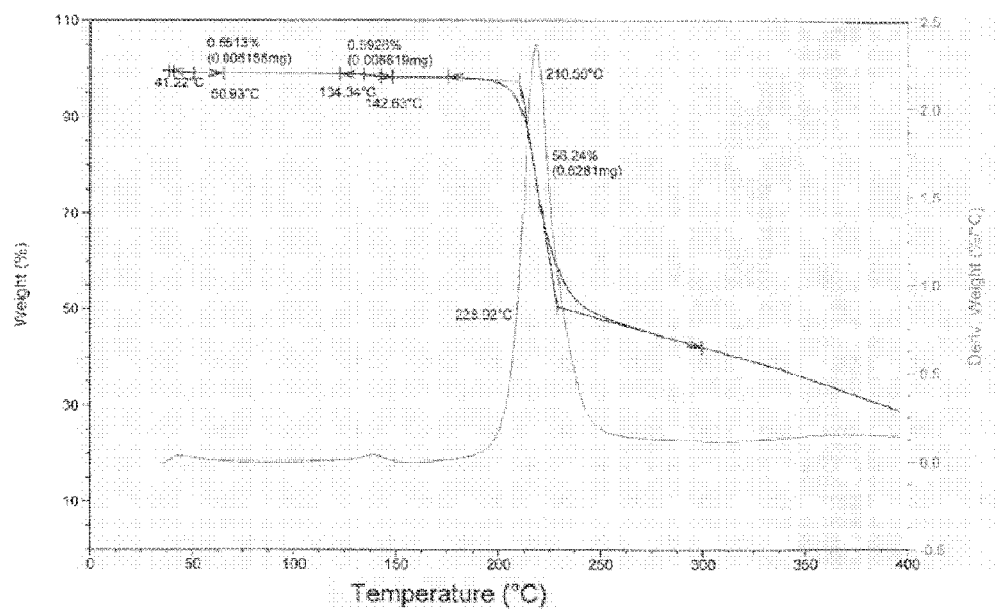
FIG. 7 shows a thermogravimetric analysis (TGA) pattern for crystalline form G of Cabazitaxel hydrate provided by example 3 of the present invention. The ordinate represents weight (mg) expressed in percentage (%), and the abscissa represents temperature expressed in ° C.
Figure 8:
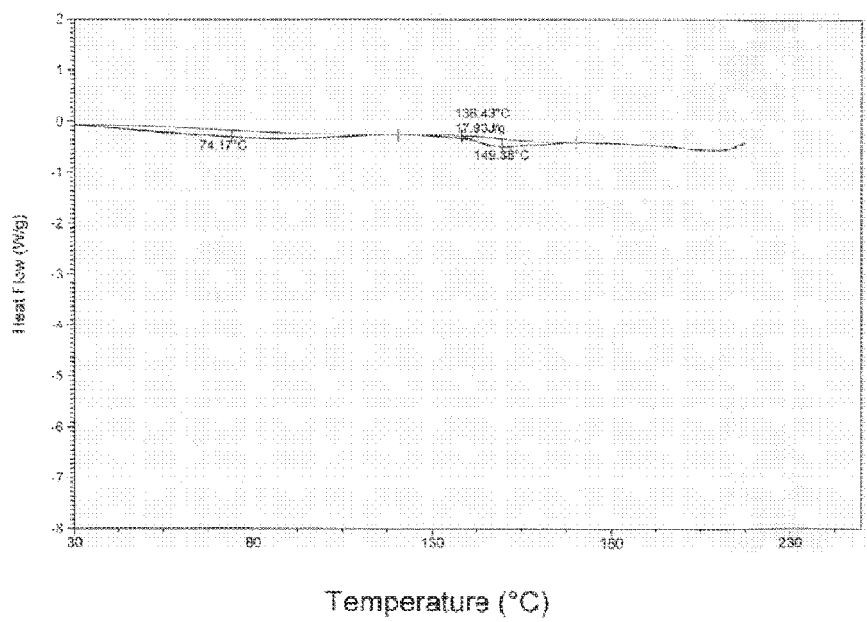
FIG. 8 shows a differential scanning calorimetry (DSC) pattern for crystalline form G of Cabazitaxel hydrate provided by example 3 of the present invention. The ordinate represents rate for heat flow expressed in cal/sec, and the abscissa represents temperature expressed in ° C.

The embodiments and examples of the present invention disclose a novel crystalline form of Cabazitaxel and the preparation method thereof, as well as the experimental data on the novel crystalline form of Cabazitaxel in terms of improving solubility and stability, respectively. In light of the present disclosure, those skilled in the art may suitably modify the process parameters to implement the present invention. It should be noted that, although the invention has been described with reference to certain specific embodiments, various modifications or combinations thereof will be apparent to those skilled in the art without departing from the spirit and scope of the invention. All such modifications as would be apparent to one skilled in the art are intended to be included within the scope of the present invention.

In order to further understand the present invention, the present invention is illustrated in detail in combination with the following embodiments and examples.

Example 1

Cabazitaxel (10 g) was added to ethyl acetate (300 mL). The mixture was heated to dissolve, concentrated till a small amount of crystalline precipitated. Then, the mixture was allowed to stand overnight for crystallization at 0 to 5° C., suction filtered, and the cake was dried under vacuum at a temperature of 50 to 60° C., to yield crystalline form J of Cabazitaxel solvate with ethyl acetate (9.4 g). The purity as measured by HPLC was ≥99.76%. The ethyl acetate residue as measured by GC was 95000 ppm. The X-ray powder diffraction pattern, infrared spectrum pattern, TGA pattern and DSC pattern thereof are shown in FIGS. 1, 2, 3 and 4, respectively.

Example 2

Cabazitaxel (10 g) was added to methyl formate (300 mL). The mixture was heated to dissolve, concentrated till a small amount of crystalline precipitated. Then, the mixture was allowed to stand overnight for crystallization at −20° C., suction filtered, and the cake was dried under vacuum at a temperature of 100° C., to yield crystalline form J of Cabazitaxel solvate with methyl formate (9.0 g). The purity as measured by HPLC was ≥199.78%. The methyl formate residue as measured by GC was 85400 ppm.

Example 3

Cabazitaxel (5 g) was added to ethyl acetate (10 mL). The mixture was heated to dissolve, concentrated till a small amount of crystalline precipitated. Then, the mixture was allowed to stand overnight for crystallization at 30 to 35° C., suction filtered, and the cake was dried under vacuum at a temperature of 30° C., to yield crystalline form J of Cabazitaxel solvate with ethyl acetate (4.4 g). The purity as measured by HPLC was ≥99.79%. The ethyl acetate residue as measured by GC was 93010 ppm.

Example 4

Cabazitaxel (5 g) was added to ethyl acetate (250 mL). The mixture was heated to dissolve, concentrated till a small amount of crystalline precipitated. Then, the mixture was allowed to stand overnight for crystallization at −20° C., suction filtered, and the cake was dried under vacuum at a temperature of 100° C., to yield crystalline form J of Cabazitaxel solvate with ethyl acetate (4.4 g). The purity as measured by HPLC was ?99.73%. The ethyl acetate residue as measured by GC was 94286 ppm.

Example 5

Cabazitaxel (5 g) was added to ethanol (75 mL) while stirring to dissolve. Then, purified water (150 mL) was added quickly dropwise. After addition, the temperature of the mixture was allowed to decrease to 8° C., stand for 2 h. Then, the mixture was filtered, and the cake was washed with purified water (200 mL) for a plurality of times, dried under reduced pressure at 60° C. for 12 h, to yield crystalline form G of Cabazitaxel hydrate as white crystalline (4.6 g). The purity as measured by HPLC was ≥99.87%. The moisture as measured by Karl Fischer method was 2.4%. The X-ray powder diffraction pattern, infrared spectrum pattern, TGA pattern and DSC pattern thereof are shown in FIGS. 5, 6, 7 and 8, respectively.

Example 6

Cabazitaxel (3 g) was added to methanol (60 mL) while stirring to dissolve. Then, purified water (150 mL) was added quickly dropwise. After addition, the temperature of the mixture was allowed to decrease to 8° C., stand for 2 h. Then, the mixture was filtered, and the cake was washed with purified water (200 mL) for a plurality of times, dried under reduced pressure at 60° C. for 12 h, to yield crystalline form G of Cabazitaxel hydrate as white crystalline (2.2 g). The purity as measured by HPLC was ≥99.83%. The moisture as measured by Karl Fischer method was 2.2%.

Example 7

Cabazitaxel (3 g) was added to isopropanol (90 mL) while stirring to dissolve. Then, purified water (180 mL) was added quickly dropwise. After addition, the temperature of the mixture was allowed to decrease to 8° C., stand for 2 h. Then, the mixture was filtered, and the cake was washed with purified water (200 mL) for a plurality of times, dried under reduced pressure at 60° C. for 12 h, to yield crystalline form G of Cabazitaxel hydrate as white crystalline (2.3 g). The purity as measured by HPLC was ≥99.7%. The moisture as measured by Karl Fischer method was 2.2%.

Example 8

Cabazitaxel (5 g) was added to methanol (250 mL) while stirring to dissolve. Then, purified water (625 mL) was added quickly dropwise. After addition, the temperature of the mixture was allowed to decrease to −5° C., stand for 2 h. Then, the mixture was filtered, and the cake was washed with purified water (100 mL) for a plurality of times, dried under reduced pressure at 100° C. for 12 h, to yield crystalline form G of Cabazitaxel hydrate as white crystalline (4.2 g). The purity as measured by HPLC was ≥99.81%. The moisture as measured by Karl Fischer method was 2.1%.

Example 9

Cabazitaxel (5 g) was added to ethanol (250 mL) while stirring to dissolve. Then, purified water (625 mL) was added quickly dropwise. After addition, the temperature of the mixture was allowed to decrease to −5° C., stand for 2 h. Then, the mixture was filtered, and the cake was washed with purified water (100 mL) for a plurality of times, dried under reduced pressure at 100° C. for 5 h, to yield crystalline form G of Cabazitaxel hydrate as white crystalline (4.3 g). The purity as measured by HPLC was ≥99.83%. The moisture as measured by Karl Fischer method was 2.4%.

Example 10

Cabazitaxel (5 g) was added to ethanol (10 mL) while stirring to dissolve. Then, purified water (25 mL) was added quickly dropwise. After addition, the mixture was allowed to stand for 5 h at a temperature of 30-35° C. Then, the mixture was filtered, and the cake was washed with purified water (100 mL) for a plurality of times, dried under reduced pressure at 30° C. for 24 h, to yield crystalline form G of Cabazitaxel hydrate as white crystalline (4.3 g). The purity as measured by HPLC was ≥99.83%. The moisture as measured by Karl Fischer method was 2.4%.

Example 11

Figure 9:
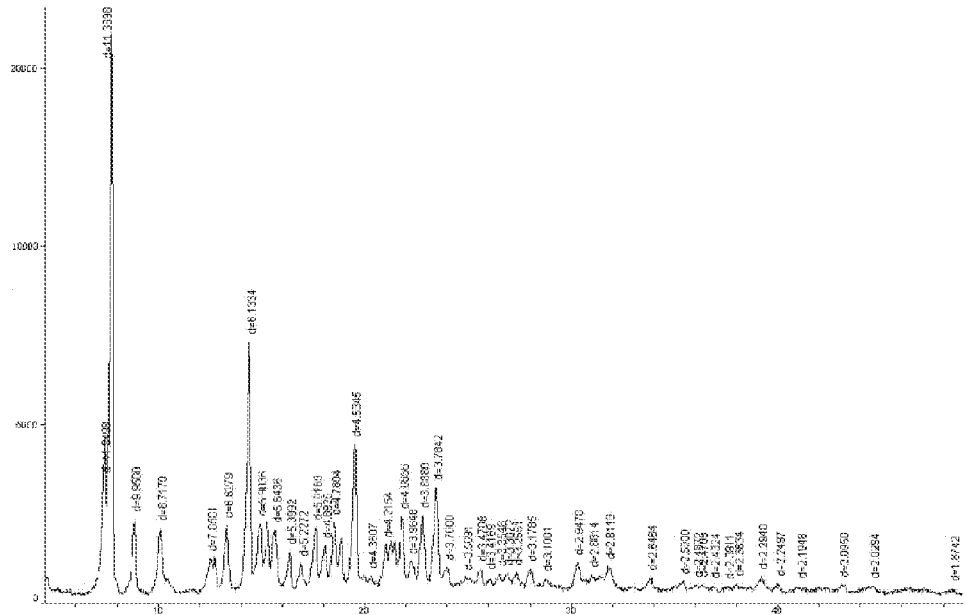
FIG. 9 shows an X-ray powder diffraction pattern for crystalline form I of Cabazitaxel provided by example 6 of the present invention, which is obtained by irradiation with cooper Kα ray. In the powder X-ray diffraction pattern, the ordinate represents diffraction intensity expressed in counts per second (cps), and the abscissa represents diffraction angle 2θ expressed in degree.
Figure 10:
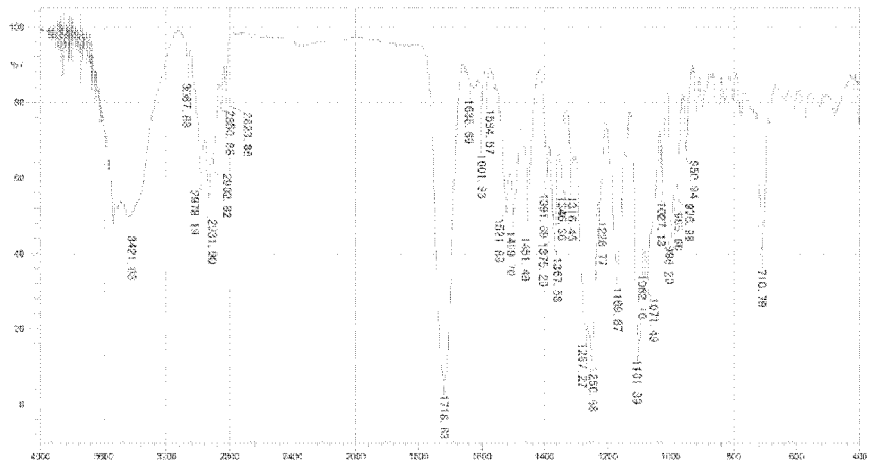
FIG. 10 shows an infrared spectrum pattern for crystalline form I of Cabazitaxel provided by example 6 of the present invention. The ordinate represents light transmittance (T) expressed in percentage (%), and the abscissa represents wave number expressed in $cm^{-1}$.

Cabazitaxel (20 g) was dissolved in methylene chloride (200 mL). Then, cyclohexane (500 mL) was added to precipitate a crystalline. Then, the mixture was allowed to stand overnight for crystallization under 0 to 5° C., suction filtered, and the cake was dried under vacuum at a temperature of 50 to 60° C., to yield crystalline form I of Cabazitaxel (17 g). The purity as measured by HPLC was ≥99.84%. The X-ray powder diffraction pattern and infrared spectrum pattern thereof are shown in FIGS. 9 and 10, respectively.

Example 12

Cabazitaxel (20 g) was dissolved in methylene chloride (1000 mL). Then, cyclohexane (2500 mL) was added to precipitate a crystalline. Then, the mixture was allowed to stand overnight for crystallization at 0 to 5° C., suction filtered, and the cake was dried under vacuum at a temperature of 50 to 60° C., to yield crystalline form I of Cabazitaxel (18 g). The purity as measured by HPLC was ≥99.86%.

Example 13

Cabazitaxel (5 g) was dissolved in ethylene chloride (5 mL). Then, cyclohexane (10 mL) was added to precipitate a crystalline. Then, the mixture was allowed to stand overnight for crystallization at 30 to 35° C. suction filtered, and the cake was dried under vacuum at a temperature of 30° C. to yield crystalline form I of Cabazitaxel (4.1 g). The purity as measured by HPLC was ≥99.83%.

Example 14

Cabazitaxel (5 g) was dissolved in isopropyl chloride (250 mL). Then, cyclohexane (500 mL) was added to precipitate a crystalline. Then, the mixture was allowed to stand overnight for crystallization at −20° C., suction filtered, and the cake was dried under vacuum at a temperature of 100° C., to yield crystalline form I of Cabazitaxel (4.4 g). The purity as measured by HPLC was ≥99.78%.

Solubility and Accelerated Stability Test for a Novel Crystalline Form of Cabazitaxel

Example 1

Solubility Test for a Novel Crystalline Form of Cabazitaxel

The obtained results are summarized in the following table 1.

TABLE 1

| Solvent | Solubility (mg/ml) | | |
|---|---|---|---|
| | crystalline form J of Cabazitaxel | crystalline form G of Cabazitaxel | crystalline form I of Cabazitaxel |
| Ethanol | 48 | 42 | 44 |
| Methylene chloride | 251 | 223 | 248 |
| Tween 80 | 67 | 63 | 67 |

Example 2

Accelerated Stability Test for a Novel Crystalline Form of Cabazitaxel

1. The results for the accelerated stability test for crystalline form J of Cabazitaxel are summarized in table 2.

TABLE 2

| Item | Time and results for the test | | | | |
|---|---|---|---|---|---|
| | 0 month | 1 month | 2 months | 3 months | 6 months |
| Moisture (%) | 0.40% | 0.44% | 0.46% | 0.50% | 0.48% |
| The other maximum individual impurity (%) | 0.08% | 0.07% | 0.07% | 0.08% | 0.08% |
| Total impurity (%) | 0.25% | 0.25% | 0.28% | 0.26% | 0.28% |
| Content (%) | 99.8% | 99.7% | 99.6% | 99.6% | 99.5% |

2. The results for the accelerated stability test for crystalline form G of Cabazitaxel are summarized in table 3.

TABLE 3

| Item | Time and results for the test | | | | |
|---|---|---|---|---|---|
| | 0 month | 1 month | 2 months | 3 months | 6 months |
| Moisture (%) | 1.92% | 1.96% | 1.99% | 2.03% | 2.09% |
| The other maximum individual impurity (%) | 0.05% | 0.05% | 0.05% | 0.05% | 0.05% |
| Total impurity (%) | 0.17% | 0.16% | 0.17% | 0.16% | 0.16% |
| Content (%) | 99.4% | 99.4% | 99.4% | 99.3% | 99.1% |

3. The results for the accelerated stability test for crystalline form I of Cabazitaxel are summarized in table 4.

TABLE 4

| Item | Time and results for the test | | | | |
|---|---|---|---|---|---|
| | 0 month | 1 month | 2 months | 3 months | 6 months |
| Moisture (%) | 0.45% | 0.47% | 0.50% | 0.54% | 0.51% |
| The other maximum individual impurity (%) | 0.06% | 0.06% | 0.05% | 0.06% | 0.06% |
| Total impurity (%) | 0.21% | 0.20% | 0.20% | 0.21% | 0.22% |
| Content (%) | 99.7% | 99.6% | 99.7% | 99.6% | 99.5% |

The illustration for the examples above is intended merely to better illuminate the method of the present invention as well as its core concept. It should be noted that various modifications and changes may be made to the invention by those skilled in the art which also fall within the scope of the invention as defined by the appended claims, without departing from the principle of the present invention.

The invention claimed is:

1. A crystalline form G of Cabazitaxel hydrate, wherein an X-ray powder diffraction pattern thereof has peaks at 2θ of about 4.5, 8.5, 8.9, 11.1, 12.4, 13.9, 15.4, 17.7 and 19.3 degrees.

2. A method for preparing a crystalline form G of Cabazitaxel hydrate, comprising:
    5 g of Cabazitaxel is added to 75 mL of ethanol while stirring to dissolve; then 150 mL of purified water is added quickly dropwise; after addition, the temperature of the mixture is allowed to decrease to 8° C., stand for 2 h; then the mixture is filtered, and the cake is washed with 200 mL of purified water for a plurality of times, dried under reduced pressure at 60° C. for 12 h, to yield crystalline form G of Cabazitaxel hydrate.

3. A method for preparing a crystalline form G of Cabazitaxel hydrate, comprising:
    3 g of Cabazitaxel is added to 60 mL of methanol while stirring to dissolve; then 150 mL of purified water is added quickly dropwise; after addition, the temperature of the mixture is allowed to decrease to 8° C., stand for 2 h; then the mixture is filtered, and the cake is washed with 200 mL of purified water for a plurality of times, dried under reduced pressure at 60° C. for 12 h, to yield crystalline form G of Cabazitaxel hydrate.

4. A method for preparing a crystalline form G of Cabazitaxel hydrate, comprising:
    3 g of Cabazitaxel is added to 90 mL of isopropanol while stirring to dissolve; then 180 mL of purified water is added quickly dropwise; after addition, the temperature of the mixture is allowed to decrease to 8° C., stand for 2 h; then the mixture is filtered, and the cake is washed with 200 mL of purified water for a plurality of times, dried under reduced pressure at 60° C. for 12 h, to yield crystalline form G of Cabazitaxel hydrate.

5. A method for preparing a crystalline form G of Cabazitaxel hydrate, comprising:

5 g of Cabazitaxel is added to 250 mL of methanol while stirring to dissolve; then 625 mL of purified water is added quickly dropwise; after addition, the temperature of the mixture is allowed to decrease to −5° C., stand for 2 h; then the mixture is filtered, and the cake is washed with 100 mL of purified water for a plurality of times, dried under reduced pressure at 100° C. for 12 h, to yield crystalline form G of Cabazitaxel hydrate.

6. A method for preparing a crystalline form G of Cabazitaxel hydrate, comprising:

5 g of Cabazitaxel is added to 250 mL of ethanol while stirring to dissolve; then 625 mL of purified water (625 mL) is added quickly dropwise; after addition, the temperature of the mixture is allowed to decrease to −5° C., stand for 2 h; then the mixture is filtered, and the cake is washed with 100 mL of purified water for a plurality of times, dried under reduced pressure at 100° C. for 5 h, to yield crystalline form G of Cabazitaxel hydrate.

7. A method for preparing a crystalline form G of Cabazitaxel hydrate, comprising:

5 g of Cabazitaxel is added to 10 mL of ethanol while stirring to dissolve; then 25 mL of purified water is added quickly dropwise; after addition, the mixture is allowed to stand for 5 h at a temperature of 30-35° C.; then the mixture is filtered, and the cake is washed with 100 mL of purified water for a plurality of times, dried under reduced pressure at 30° C. for 24 h, to yield crystalline form G of Cabazitaxel hydrate.

\* \* \* \* \*